United States Patent
Laino et al.

(10) Patent No.: US 8,187,879 B2
(45) Date of Patent: May 29, 2012

(54) COLLECTION AND SELECTION METHODS TO ISOLATE A STEM CELL POPULATION FROM HUMAN ADULT PERIODONTAL FOLLICULAR TISSUES

(75) Inventors: Gregorio Laino, Torre del Greco (IT); Gianpaolo Papaccio, Naples (IT); Alfredo De Rosa, Naples (IT); Riccardo D'Aquino, Naples (IT); Antonio Graziano, Naples (IT)

(73) Assignee: Teslab S.R.L., cava de' tirreni ( * ) Notice: Subject to any disclaimer, the term of this patent is extended or adjusted under 35 U.S.C. 154(b) by 799 days.

(21) Appl. No.: 12/279,853

(22) PCT Filed: Feb. 19, 2007

(86) PCT No.: PCT/EP2007/001416
§ 371 (c)(1),
(2), (4) Date: Dec. 19, 2008

(87) PCT Pub. No.: WO2007/096115
PCT Pub. Date: Aug. 30, 2007

(65) Prior Publication Data
US 2009/0291065 A1    Nov. 26, 2009

(30) Foreign Application Priority Data
Feb. 20, 2006 (IT) .............................. NA2006A0017

(51) Int. Cl.
C12N 5/00 (2006.01)
C12N 5/02 (2006.01)
C12N 5/071 (2010.01)

(52) U.S. Cl. ......... 435/378; 435/381; 435/384; 435/366

(58) Field of Classification Search .................. 435/378, 435/381, 384, 366
See application file for complete search history.

(56) References Cited

FOREIGN PATENT DOCUMENTS
WO    WO 03066840 A2 *  8/2003

OTHER PUBLICATIONS

Morsczeck and Schmalz. J. of Dental Res., 89(4): 445-456, 2010.*
Tomic et al. Stem Cells and Development, 20(4): 695-708, 2011.*
Morsczeck et al. Matrix Biology, 24: 155-165, 2005.*
"Cell Culture Newsletter" from Sigma, Summer, 2004, pp. 1-22.*
Gronthos et al., "Postnatal Human Dental Pulp Stem Cells (DPSCs) in Vitro and in Vivo", PNAS 97(25):13625-30 (2000).
Shi et al., "Comparison of Human Dental Pulp and Bone Marrow Stromal Stem Cells by cDNA Microarray Analysis," Bone 29(6):532-39 (2001).
Ulloa-Montoya et al., "Culture Systems for Pluripotent Stem Cells", J Biosci Bioeng 100(1):12-27 (2005).
Laino et al., "A New Population of Human Adult Dental Pulp Stem Cells: A Useful Source of Living Autologous Fibrous Bone Tissue (LAB)", J Bone Min Res 20(8):1394-1402 (2005).
Gronthos et al. "Stem Cell Properties of Human Dental Pulp Stem Cells", J Dent Res 81(8):531-35 (2002).
D'Aquino et al., "Human Neural Crest-Derived Postnatal Cells Exhibit Remarkable Embryonic Attributes Either in Vitro or in Vivo" European Cells and Materials 21:304-316 (2011).

* cited by examiner

*Primary Examiner* — Thaian N Ton
(74) *Attorney, Agent, or Firm* — Porzio, Bromberg & Newman, P.C.

(57) ABSTRACT

Methods for the isolation, expansion and storage of a population of stem cells belonging to human dental follicles, called FENC (Follicle-derived Embryonic Neural Crest stem cells,) including: a) Collection of the follicular sack in sterile conditions, digestion and primary culture growth and expansion; b) Optional amplification; c) FACsorting.

6 Claims, No Drawings

COLLECTION AND SELECTION METHODS TO ISOLATE A STEM CELL POPULATION FROM HUMAN ADULT PERIODONTAL FOLLICULAR TISSUES

SUMMARY

This invention concerns of a new method for the isolation of a new stem cells subpopulation from human dental follicle with embryonic-like antigenic characteristics, as well as of a method for the expansion thereof culture: The isolated cells can be characterized and stored in cell collections for experimental and therapeutic uses.

More particularly, the invention describes: 1) Isolation of stem cells from periodontal follicular tissues from donor; their growth in vitro, in particular culture conditions able to allow the isolation of embryonic-like; their banking in order to preserve the viability; their differentiation towards different cytotypes; the use of isolated stem cytotype for cell therapies and/or tissue engineering on the donor itself or HLA-compatible host, to regenerate injuries of various aetiology.

BACKGROUND OF THE INVENTION

The chance to isolate stem cells form human tissues today is controversial and much-discussed. The definition itself of stem cell, a cell able to self-renew and differentiate towards all the different cytotypes of the organism from which it derives, does not fit with the antigenic and functional characteristics of the adult stem cells, up to now collectable in humans after the birth. On the side of the "self-renewing", actually, adult stem cells that have been isolated up to now, do not display unlimited proliferation ability and, on the other side, differentiation ability has been hardly overcome the multipotency (the ability to differentiate in all the cytotypes that come from the same germinal layer) or pluripotency (the ability to differentiate in the cytotypes that come from different germinal layers too), without reaching the totipotency (the ability to differentiate in every cytotype); the latter is an ability owned by zygote and by cells of the blastocyst, leading to the first steps of human development. On the other hand, the chance to handle cells collected from human embryos for therapeutic and research applications often collides with technical, ethic and legal difficulties. For these reasons the chance to isolate in adult humans undifferentiated cytotypes, represents not only an interesting experimental model of cellular differentiation and for cancer related issues, but also an important therapeutic tool to cure tissue degeneration-based diseases, caused by quantitative and qualitative defects.

The stem cells are cytotypes characterized by:
1) unlimited self-renewal;
2) differentiation ability towards numerous cytotypes.

With respect to the prior art, represented by WO 03/066840 that includes follicular cerotype, this invention shows the following differences:
1) Antigenic pattern and selection methods of the cells. WO 03/066840 does not disclose any selection, whereas the method of the invention uses selection by cytofluorimetry of embryonic stem cells, through antigens detection such as SSEA-4, TRA 1-60, TRA 1-81, CD133, CD90, flk-1. In this way it is possible to obtain a homogeneous population of embryonic cells.
2) Culture methods, cellular proliferation and differentiation; actually WO 03/066840 describes the techniques to collect a cellular population that contains only in a small part adult stem elements, whereas the selection method according to the present invention allows the preparation of an homogeneous embryonic-like stem cells population.

SUMMARY OF THE INVENTION

The invention describes a method for isolating from the follicular sack a new non-haematopoietic, mesenchymal stem subpopulation, herein after referred to as FENC (Follicle-derived Embryonic Neural Crest stem cells), by means of FACsorting selection, after suitable staining with specific antibodies.

The invention also provides culture and proliferation methods of FENC. The cells obtainable by the method of the invention are able to differentiate in all the tissues from the three germinal layer, thus making FENCs a totipotent/multipotent cell population. FENC may be stored preserving their viability, so that it is possible to establish cellular banks to store embryonic stem cells collected from adult patients. The invention also provides methods for cell and/or genomic therapy by means of FENCs as well as clinical therapeutical application of cells and tissues obtained from FENCs differentiation.

DETAILED DESCRIPTION OF THE INVENTION

The invention concerns a method for the isolation of a new cytotype of embryonic stem cells collected from human adults, in particular a method for the isolation of these cells, including the collection thereof from follicular sack.

The dental follicle, as the tissue complex that embraces the tooth during its formation before the eruption, represents a privileged source of undifferentiated cells due to two reasons:
1) Each tooth, both permanent and deciduous, represents an incomplete organ at the birth. It brings in its development site undifferentiated cells that, after proliferation, will become odontogenic cells. The embryonic origin, from the neural crests, explains their immaturity. At the end of odontogenesis too, these undifferentiated cell remain in loco up to the eruption, within the follicle, because they will become the future cells of periodontium and root apexes that develop after the eruption. It is now certain the presence of adult stem cells within periodontal ligament (Gronthos, Lancet 2004), and within the dental pulp (Gronthos, PNAS 2000; Miura, PNAS 2003; Laino, JBMR 2005).
2) The dental follicle is a biological niche with an easy surgical access, as well as with a high ratio between undifferentiated stem cells and collected tissue volume. The tissue sacrifice for stem cell collection is minimal because the extraction of the wisdom teeth is very frequent and requires the collection of the follicular sack. The stem cells, having embryonic characteristics obtained from these biological samples, can be stored for research and autologous therapeutic applications.

These cells derive from neuro-ectoderm and express differentiation ability in the cytotypes originated from this layer.

The invention provides for the first time the isolation of an homogeneous cell population with embryonic characteristics from human adults.

This strategy presents these advantages: 1) low-invasive surgery with local anaesthesia; 2) low morbidity of the site; 3) high-clonogenic mesenchymal culture, due to the absence of hematopoietic fraction; 4) isolation of embryonic cells from human adults.

Obtaining of FENCs—the stem cells obtained from follicular sack directly derive from mesenchymal cells originated in the neural crests during organogenesis. Their origin explains their plasticity. To isolate stem cells from the follicular sack, the latter must be intact with no communication with the oral cavity.

The patient, during the week before the surgery, must follow a suitable oral hygiene protocol, e.g. rinsing the oral cavity at least twice a day with CHX 0.12 or similar agents.

For the follicular sack collection, after anaesthesia, the flap is cut and a bone door is opened to reach the impacted tooth, embraced by the follicular sack. Once collected in sterile conditions, the sample is immersed in a digestive solution for 1 hour at 37° C. At the end of the first hour, the digestive solution is filtered to eliminate cell aggregates and ECM particles. After this, the digestive process is stopped and the cells are cultured, (in Mega Cell medium (SIGMA-Milan, Italy). Alternatively, the medium for the embryonic stem cells (ES) may be used. Microscope observations evidence that, starting from the first day of culture; it is possible to obtain a good number of cells, adherent to the bottom of the flasks, that give origin to clones. After 5 days in a 75 ml flask it is possible to count up to 60 clones.

At the 9°-10° day, after removal of surnatant, cells are challenged at the FACsorting, collecting the cell clones positive for stem markers.

The isolated FENCs differentiate, with or without stimulation, in different cytotypes. It is possible to obtain proliferation without differentiation adding βFGF to the culture medium.

After the cells reached a suitable number, they may be frozen and stored in liquid nitrogen at −80° C.

The procedure is summarized below:
1) Collection of the follicular sack in sterile conditions, digestion and culture;
2) Amplification of primary cultures, if necessary;
3) FACsorting;
4) Amplification, freezing and/or cell differentiation;
5) FACanalysis;
6) Maintaining in an undifferentiated condition;
7) Tissue engineering from differentiated cells.

All the cell types obtained from FENCs differentiation, can be used not only in cell therapy but also to build different tissues.

For instance the FENC may be used to obtain osteogenic precursors, expressing RUNX-2, from which derive osteoblasts expressing HLA-1, CD44, RUNX-2 e CD54 and osteocalcin.

An osteoid matrix called LAB (Living Autologous Bone) may also be obtained from osteoblasts, expanded and cryopreserved. LAB is made of bone tissue samples, having a thickness of more than 1 cm and a volume of more than 1 cm$^3$. LAB formation, containing osteoblasts that actively produce bone is characterized by: 1) cluster formation that secrete within a central area inorganic crystals, collagen fibers and glycoproteins; 2) 3D organization of this structure building a mineralized bone matrix.

Said LAB is formed by growing the cells at 37° C. in an atmosphere of 5% $CO_2$ using α-MEM culture medium, added with 20% p/v FBS, 100 μM 2P-ascorbic acid, 2 mM L-glutamine, 100 U/mL penicillin, 100 μg/mL streptomycin. LAB formation is only blocked due to a lack of nutrients.

Said LAB may be produced continuously and the osteoid tissue can be stored, maintaining the osteoblasts at 4° C. or at temperatures<0° C., using the common techniques of cell cryopreservation.

A 3D matrix containing LAB may also be obtained, in which osteoblasts are grown in presence of a 3D biocompatible matrix, that is colonized by cells. Said biocompatible matrix may be reabsorbable or not in vivo: examples of suitable the matrices comprise lactide co-glycolic acid, synthetic collagens, HA, biocorals, calcium sulphate, while those not reabsorbable by polymethacrylates, PTFe, titanium, compact HA, HA biphasic (50% HA and 50% of β-TCP), ceramic.

According to a further embodiment of the invention, FENC may also be differentiated to myoblasts, in order to obtain smooth muscle cells using Mega Cell culture medium with FBS p/v 2%, 100 μM 2P-ascorbic acid, 2 mM L-glutamine, 100 U/mL penicillin, 100 μg/mL streptomycin added with 10 ng/ml TGFβ.

FENC may also be differentiation in vitro to myoblasts, in order to obtain striated muscle, using a co-culture with C2C12 murine myotubes. Co-culture is carried out using a 1:10 ratio for 7 days, using as the following culture medium: Dulbecco's modified Eagle's medium (DMEM, Invitrogen), with 4 mM L-glutamine, 1.5 g/L sodium bicarbonate, 4.5 g/L glucose and 1.0 mM sodium pyruvate added with FBS 10%.

FENC may also be differentiated in vitro to neurons and glial cells, using a culture of 15-30 days in Neurobasal A (Invitrogen, Milano, Italy), added with B27 protein (Invitrogen, Milan).

The glial cells from neurons obtained by FENC differentiation may be selected by FACsorting using the anti-GFAP antibody for glial cells.

FENC may also be differentiated into adipocytes, by culturing for 30 days in α-MEM, added with 20% p/v FBS, 100 μM 2P-ascorbic acid, 2 mM L-glutamine, 100 U/mL penicillin, 100 μg/mL streptomycin, $10^{-8}$ M dexamethason.

Chondrocyte differentiation of FENC, in order to obtain cartilage, may be obtained culturing FENC cells for 30 days using α-MEM, added with 20% p/v FBS, 100 μM 2P-ascorbic acid, 2 mM L-glutamine, 100 U/mL penicillin, 100 μg/mL streptomycin reducing $pO_2$<40 mmHg.

The invention allows the autologous use of FENC in cell therapy protocols.

In particular, the autologous use of FENC and cells derived from them may be useful in the following applications:
  skeletric apparatus pathologies like bone defects by means of FENC-derived-osteoblasts.
  muscular tissue degeneration, both of smooth and striated muscular tissue, by means of FENC-derived myoblasts.
  CNS pathologies by means of FENC-derived neurons.
  myeline degeneration by means of FENC-derived glial cells
  in plastic surgery, when the formation of adipous tissue is desired, by means of FENC-derived adipocytes.
  in oncological and plastic surgery fields, by means of FENC-derived chondrocytes.

Cancerogenesis tests—To rule out cancerogenesis, FENCs and differentiated cells therefrom have been injected in nude mice, after infection with lentivirus III (Invitrogen, Milano, Italia), by means of a vector comprising GFP (green fluorescence protein) cDNA. After transplantation, the animals were followed for 30 days and sacrificed. Histological observations both on the transplantation site and on the main organs, evidenced no cancer development.

Cells have been challenged for main cancer markers and for cell cycle analysis: all the cells were euployd with no cancer evidence.

Some examples of FENCs applications are reported below.

Example 1

Cell Isolation and Culture

Each healthy patient, starting from the week before the surgery, was subjected to mouth rinsing treatment with CHX 0.12 w/v twice a day. For the follicular sack collection, after local anaesthesia, the flap was cut and a bone door was opened to reach the impacted tooth, embraced by the follicular sack. Once collected in sterile conditions with a Gracey curette or an alveolar spoon, the sample was immersed in a digestive solution for 1 hour at 37° C. The digestive solution was PBS (phosphate buffer solution pH 7.4 1M) containing 3 mg/mL of collagenase type I, 4 mg/mL Dispase, 100 U/mL penicillin, 100 μg/mL of streptomycin and 500 μg/mL clarytromicin.

The volume of the solution depended on the volume of the follicular sack collected, and ranged from 8 to 15 mL. The samples were kept in the solution for 1 hour at 37° C. At the end of the first hour, the digestive solution was filtered with Falcon® strainer 70 μm to remove the fragments of ECM, cells or big aggregates. The sample was digested again for 30' if tissue fragments were still present. To stop the digestion, a volume equal to ten times the volume of the digestion were added to the digestive solution and centrifuged for 10' at 140 g. The culture medium was Mega Cell (SIGMA, Milan, Italy), added with 10% w/v foetal bovine serum (FBS), 100 μM 2P-ascorbic acid, 2 mM L-glutamine, 100 U/mL penicillin, 100 μg/mL streptomycin. At the end of centrifugation from the bottom of the tube, 25 ml of the suspension were collected and cultured in a 50 ml flask at 37° C. and 5% $CO_2$, changing the culture medium twice a week. Microscopical observations evidenced that, starting the first day of culture, adherent cells gave origin to cell clones.

Example 2

Growth and Characterization

After 5 days of culture in the medium described above or embryonic medium (ES medium, Invitrogen, Milan, Italy) in 75 flasks up to 60 clones were counted.

At the 9°-10° day, after removing the surnatant and washing with sterile PBS, cells were detached from the bottom of the flasks. 4 mL of EDTA 0.02%, dissolved in PBS Mg/Ca free, for 10' at 37° C. and a FACsorting was performed, collecting the cell clones positive for stem markers. Cells were pelletted (10' at 140 g), washed in BSA (Bovine Serum Albumin) 0.01% in PBS at 4° C. and incubated for 30' at 4° C. for staining with 10 μl stock solution antibody. After incubation, cells were washed once with 1 ml of BSA 0.1% in PBS, to remove not reactive or aspecific antibodies, and analyzed for positivity to the following antibodies: SSEA-4, TRA 1-60, TRA 1-81, CD133, CD90, flk-1 (Santa Cruz, Calif., USA). The cells were positive for SSEA-4 in a percentage of 70% and of 80% for TRA 1-60 and TRA 1-81. In particular SSEA-$4^+$ were positive both for TRA 1-60 and TRA 1-81. SSEA-4, TRA 1-60 and TRA 1-81 are surface molecules present only on undifferentiated cells, or on Embryonic Stem Cells (ES totipotent) and Embryonic Germ Cells (EG pluripotent). After sorting a small sample was challenged for 3 transcription factors, Nanog, OCT-4 e Rex-1, that are usually detectable only on embryonic undifferentiated cells. The positivity for the previous antigens confirms the embryonic nature of the cells (ES) (Zhang Nature 2003). OCT-4 positivity was 100% in all sorted cells. For Nanog e Rex1 analysis, after obtaining a suitable number of cells, RNA was isolated and analyzed with RT-PCR.

Example 3

Differentiation Type a (Bone, Smooth Muscle and Cartilage)

FENCs, isolated e characterized as reported in examples 1 e 2, can differentiate, with or without stimulation, or can proliferate restraining the differentiation, adding 8 ng/mL βFGF to the culture medium.

For the osteogenic differentiation, the cells can be cultured with α-MEM, with FBS 20% w/v, 100 μM 2P-ascorbic acid, 2 mM L-glutamine, 100 U/mL penicillin, 100 μg/mL streptomycin. The cells differentiate in osteoblasts in about 25 days, building woven bone (positive for antibodies anti-collagen type I and III, osteocalcin, osteonectin, BAP).

For smooth muscle differentiation FENCs must be cultured with 2% Mega Cell (SIGMA) FBS p/v, 2P-ascorbic acid 100 μM, L-glutamine 2 mM, penicillin 100 U/mL, streptomycin 100 μg/mL adding 10 ng/ml TGFβ. In these conditions cells differentiate in about 4-5 days and become positive for SMA antibody-staining, marker of smooth muscle differentiation.

For cartilage differentiation, FENCs were cultured in α-MEM medium, adding 20% w/v FBS, 100 μM 2P-ascorbic acid, 2 mM L-glutamine, 100 U/mL penicillin, 100 μg/mL streptomycin reducing $pO_2$<40 mmHg and cultured at 37° C. with 5% of $CO_2$. Cartilage building, thanks to the high cell concentration (500.000/15 mL) occurs in about 30 days and can be verified by analysis of Collagenase Type II expression.

Example 4

Differentiation of Type b (Neurons and Glial Cells)

Follicular cells can differentiate either spontaneously or using the Neurobasal A medium (Invitrogen, Milan, Italy), added of B27 protein (Invitrogen, Milan, Italy). The culture was followed for 5-7 days. In both cases a great number of differentiated neurons and glial cells was obtained. A cytofluorimetric assay using an anti-GFAP antibody may then lead to select and isolate the two cytotypes. Actually, differentiated cells are:
  glial cells when positive for the GFAP antibody;
  neurons when positive for the anti-TuJI, anti-neurofilament, anti-Brn3A (a transcriptional factor) antibodies;
  peripheral neurons when positive for anti-peripherin and anti-p75 antibodies.

Example 5

Differentiation of Type c (Striated Muscle, Adipocytes)

The differentiation of FENC into striated muscular cells can be achieved by means of co-culture with C2C12 murine myotubes. The co-culture was made using the percentage of 1:10, using known methods (e.g. Laino et al., 2006), in a medium made as follows: Dulbecco's modified Eagle's medium (DMEM, Invitrogen), added with 4 mM L-glutamine, 1.5 g/L sodium bicarbonate, 4.5 g/L glucose, 1.0 mM sodium piruvate, and FBS 10% for a week. After co-culture, the percentage of FENC fused within murine myotubes was calculated by means of anti-human nuclear laminin. Usually, the percentage of fusion was of about 15-20%. Fused myotubes can be used for transplantation.

Adipocyte differentiation was obtained adding dexamethasone $10^{-8}$ M for 30 days in the following culture medium: α-MEM, added with FBS 20% p/v, 100 μM 2P-ascorbic acid, 2 mM L-glutamine 2 mM, 100 U/mL penicillin 100 U/mL, 100 μg/mL streptomycin. At the end, numerous adipocytes could be observed which could be stained with Sudan black or, freshly, with Oil red-O.

Adipose cells can be used for plastic surgery.

Example 6

Tissue Engineering and Clinical Application

FENC, once differentiated, can be used for tissue reconstruction also by means of rotative cultures, in a Roller apparatus. Osteoblast differentiated cells, for instance, can be plated on lactide coglycolyc (85:15) scaffolds (that is reabsorbable within 15 days). Rotating cultures (⅕ sec.) are made in a 5% $CO_2$ incubator for 30 days. Once the tickness of 1 cm is reached, the 3D tissue structure was observed and evaluated by means of histological, immunohistochemical and SEM techniques.

Bone tissue can be used for defect regeneration. If these cells can be obtained from the patient, a scaffold may be modelled and the 3D culture can be made. After 20-30 days, the complex scaffold-cells is ready to be implanted in the patient's locus.

Graft may be done using standard surgical techniques. Preparing the locus for transplantation involves to create a conspicuous blood extravasation and reduce the cortex layers. Therefore the scaffold-cells integration with host may be made easier and the transplantation may then be carried out.

The perfect integration was achieved in 40-60 days.

Tissue repair can be achieved thanks to this autologous technique using stem cells.

Terminology

Mega cell=culture medium for cells (Sigma-Aldrich, Milan, Italy)
ES=culture medium (Invitrogen, Milan, Italy)
βFGF=beta fibroblast growth factor
α-MEM=alpha Medium Essential Medium (Invitrogen)
anti-GFAP=antibody directed against the glial fibrillar acid protein
GFAP=Glial Fibrillar Acid Protein
SMA=Smooth Actin
TGFβ=Tumor Growth Factor β
BAP=Bone Alkaline Phosphatase
βFGF=Fibroblast Growth Factor β
RT-PCR=Reverse Transcriptase Polymerase Chain Reaction
Nanog=Transcription factor of embryonic cells during the early development
Rex1=Transcription factor of embryonic cells during the early development
OCT-4=Octamer 4
SSEA-4=Stage-specific embryonic antigen
TRA 1=Tumor rejection antigen-1
CD=Cluster of differentiation
flk-1=Foetal Liver Kinase-1
HA=hydroxyapatite
TCP=tricalcium phosphate

The invention claimed is:

1. A method for the isolation of a population of stem cells from human dental follicles comprising:
   a) collecting intact human dental follicular sacks;
   b) digesting the follicular sacks in sterile conditions to produce a digestive solution;
   c) filtering and then centrifuging the digestive solution to produce a cellular suspension;
   d) isolating the cellular suspension;
   e) culturing the cellular suspension in a culture media specific for stem cells to produce a primary culture;
   f) optionally allowing the cells in the primary culture to amplify;
   g) isolating stem cells by FACsorting using antibodies against SSEA-4, TRA 1-60, TRA1-81, CD133, CD90, flk-1, and OCT-4.

2. The method according to claim 1, in which the digestion is carried out using proteolytic enzymes and antibiotics.

3. The method according to claim 2, in which the enzymatic digestion is carried out by means of an aqueous solution containing: 3 mg/mL type I collagenase, 4 mg/mL dispase, 100 U/mL penicillin, 100 μg/mL streptomycin, 500 μg/mL clarytromicin in PBS.

4. The method according to claim 3, in which the enzymatic digestion is carried out for 1 hour at 37° C., under shaking.

5. The method according to claim 1, in which the culture media is supplemented with 10% p/v FBS, 100 μM 2P-ascorbic acid, 2 mM L-glutamine, 100 U/mL penicillin, 100 μg/mL streptomycin.

6. The method according to claim 5, in which the incubation is carried out at 37° C. and in an atmosphere of 5% $CO_2$ for 15-20 days, changing the medium every 3 days.

* * * * *